(12) United States Patent
Cutlip

(10) Patent No.: US 7,256,390 B1
(45) Date of Patent: Aug. 14, 2007

(54) INFLATABLE SPHERICAL INTEGRATING SOURCE FOR SPACEFLIGHT APPLICATIONS HAVING A REFLECTIVE INTERIOR SURFACE

(75) Inventor: Hansford H. Cutlip, Buellton, CA (US)

(73) Assignee: Raytheon Company, Waltham, MA (US)

( * ) Notice: Subject to any disclaimer, the term of this patent is extended or adjusted under 35 U.S.C. 154(b) by 33 days.

(21) Appl. No.: 11/282,511

(22) Filed: Nov. 18, 2005

(51) Int. Cl.
*G01J 1/00* (2006.01)

(52) U.S. Cl. ...................... 250/228; 250/239

(58) Field of Classification Search ................ 250/228, 250/239, 559.1, 221; 356/236, 241.1
See application file for complete search history.

(56) References Cited

U.S. PATENT DOCUMENTS

| | | | |
|---|---|---|---|
| 3,592,157 A * | 7/1971 | Schwartz | 340/815.74 |
| 5,044,579 A | 9/1991 | Bernasconi et al. | 244/158 R |
| 5,202,689 A | 4/1993 | Bussard et al. | 342/10 |
| 5,302,823 A | 4/1994 | Franklin et al. | 250/252.1 |
| 6,927,850 B1 | 8/2005 | Snail et al. | 356/244 |

OTHER PUBLICATIONS

"Spectral Radiance of a Large-Area Integrating Sphere Source", James H. Walker et al., Journal of Research of the National Institute of Standards and Technology, vol. 100, No. 1, Jan.-Feb. 1995, pp. 37-41.

* cited by examiner

*Primary Examiner*—Que T. Le
(74) *Attorney, Agent, or Firm*—Leonard A. Alkov

(57) ABSTRACT

A system for calibrating a sensor in a vehicle, such as a space capsule or other space borne apparatus, uses an expandable integrating sphere. A sensor in the vehicle measures the energy from an electromagnetic energy source within the integrating sphere through a calibration window. The expandable fluid impermeable integrating sphere expands when filled with a fluid, such that when filled with the fluid, its interior is viewable through the calibration window. The system includes a source of fluid to fill the integrating sphere and a fluid regulator coupled to the vehicle to determine when to supply the fluid to the integrating sphere to maintain an appropriate gas pressure level with the integrating sphere.

16 Claims, 5 Drawing Sheets

INFLATABLE SPHERICAL INTEGRATING SOURCE FOR SPACEFLIGHT APPLICATIONS HAVING A REFLECTIVE INTERIOR SURFACE

FIELD OF THE INVENTION

The present invention relates to spatially uniform radiometric calibration sources for instrument and sensor calibration and, more particularly, to optical spherical integrating sources.

BACKGROUND OF THE INVENTION

Space based remote sensing is an accepted means used to study various topics of scientific interest including global warming and climate change studies, and conditions on and around planets, natural satellites, asteroids, comets, and other astronomical objects of interest. Radiometric calibration maximizes the usefulness of data collected via space based radiometry.

Many space based sensors that work in the visible spectrum utilize diffusing plates that use solar irradiance as their primary on-board source of radiometric calibration. However, this is not always possible due to the lack of clear lines of sight to the sun, stray light, or other reasons. Spacecraft on an interplanetary trajectory also cannot use the standard techniques because the local solar irradiance is a function of distance from the sun, and that distance is constantly changing. Further, required access to sunlight for calibration purposes may not be available due to spacecraft structure, other payloads, antennas, or fixed attitude constraints. Rapidly changing angles of incidence may greatly complicate the use of the sun as a source of radiometric calibration.

Spaced based sensors that work in the infrared (IR) spectrum usually employ on-board blackbody simulators that produce calibrated radiances. The spectral radiance produced by an on-board blackbody is a function of the temperature of the blackbody. If higher or lower spectral radiances are required, the temperature of the blackbody is raised or lowered. This change in temperature also changes the spectral shape or color temperature of the radiance emitted, which may be undesirable for sensors that have passbands in a steeply sloped region of the spectrum.

An integrating sphere allows the production of different radiance levels without also changing the color temperature of the emitted radiance. An example of an integrating sphere used in a space borne application is found in Franklin et al., U.S. Pat. No. 5,302,823. Other references relating to integrating spheres include Snail et al., U.S. Pat. No. 6,927,850, and an article entitled "Spectral Radiance of a Large-Area Integrating Source," James H. Walker et al., Journal of Research of the National Institute of Standards and Technology, Vol. 100, No. 1, January-February 1995, pp. 37-41. Walker's article discloses larger sized integrating spheres provide radiometric measurements of higher accuracy.

Of concern in performing calibration measurements with an integrating sphere in constrained environments is the volume taken up by the integrating sphere.

SUMMARY OF THE INVENTION

In a first aspect of the present invention, an optical spherical integrating source includes a structure that expands to provide a spherical shape, the structure having an open interior when expanded, characterized by a reflective surface and a source of visible or infrared radiance to illuminate the interior of the expandable structure.

In a second aspect of the present invention, a system for calibrating an optical remote sensor in a spacecraft includes a sensor; a calibration window; an expandable gas impermeable integrating sphere that expands when filled with a gas, the integrating sphere being disposed such that when filled with the gas its interior is viewable through the calibration window; and a source of gas to inflate the integrating sphere.

In a third aspect of the present invention, a method for deploying an optical integrating sphere includes securing an expandable and unexpanded optical integrating sphere to a vehicle over a calibration window of the vehicle and, upon reaching an intended vehicle destination, expanding the optical integrating sphere with a fluid. The internal pressure of the optical integrating sphere may be maintained by a regulator and fluid supply.

BRIEF DESCRIPTION OF THE DRAWINGS

A better understanding of the present invention will be realized from the detailed description which follows, taken in conjunction with the accompanying drawings, in which.

DETAILED DESCRIPTION OF THE INVENTION

Figure 1:
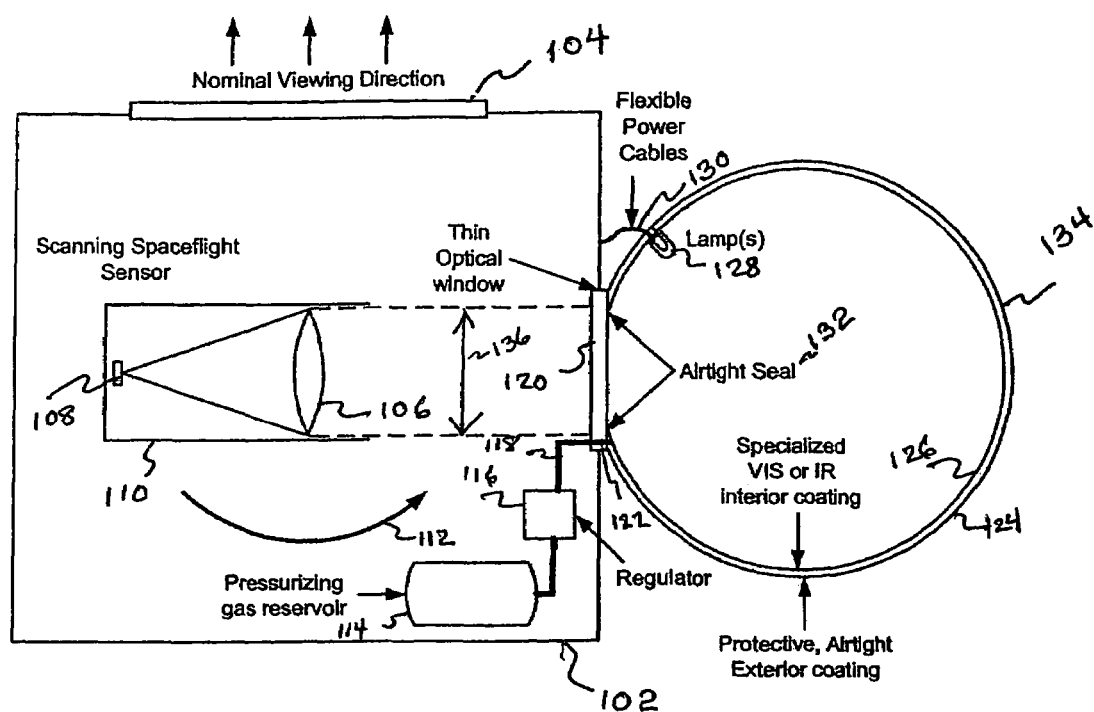
FIG. 1 shows an expandable integrating sphere in operating mode with vehicle.

The present invention relates to a space saving method and apparatus for providing an integrating sphere for a vehicle, such as a space capsule or satellite in orbit around the earth or on an interplanetary trajectory. The integrating sphere may be secured to or within the vehicle, such as a satellite body, a probe body, a space capsule body, an instrumentation package, or the like. In a space borne environment, the integrating sphere may be direct exposure to space, or it may be housed within a pressurized capsule. The present invention is not limited to extraterrestrial environments, but may also be used for various airborne, surface, submersible, and subterranean implementations. An integrating sphere for calibrating instrumentation has an expandable structure that expands to allow measurements of radiated energy within its interior, an aperture in the expandable structure to permit inflating fluid (gas or liquid or a material that converts to a gas or liquid state) to fill the expandable structure and thereby expand the expandable structure, and a source of electromagnetic energy to irradiate the interior of the expandable structure. The integrating sphere is made of preferably stretchable or balloon-like material, or it may be a fixed surface area material folded up like an automotive air bag. By using the expandable integrating sphere, space based instruments may take advantage of established laboratory techniques that have previously been unavailable to space instruments primarily due to constraints on available volume and mass for instrumentation. The inflatable integrating sphere may further aid ground personnel in diagnosing problems that arise when the satellite or space capsule is space borne. A preferred launch configuration is with the sphere deflated, folded, and secured to conform to launch related volume restrictions. Once in orbit, a fluid, such as an inert gas, that is stored in a compressed gas cylinder (or other fluid source) inflates the sphere to a pressure that is high enough to keep the sphere at least roughly spherical. The interior is well sealed to preventing outgassing from the pressurizing gas. The integrating sphere is preferably opaque to electromagnetic energy frequencies that may damage the interior coating. The interior coatings may be different for visible and infrared applications and may be formed of polymer or metallicized synthetic material. The interior coating provides diffuse high reflectance material and may have either a smooth or a non-smooth, e.g., a crinkled surface.

In an exemplary embodiment, the present invention uses a standard optical window on the vehicle for calibrating a sensor. The expandable structure of the integrating sphere is collapsible, foldable, or otherwise highly packable to permit, for example, a greater than 10 times volume reduction between a storage state and a deployment state and is highly scalable in size (e.g., centimeters through meters). The integrating sphere accepts various broadband and narrowband illumination sources such as incandescent lamps, light emitting diodes, infrared sources, and laser light sources, and may use calibrated trap detectors for lamp stability.

FIG. 1 shows a deployed exemplary configuration of an inflated or expanded integrating sphere 134 affixed to a vehicle 102, such as space borne satellite. A sensor 108 is located at a closed end of a container 110. Light may pass through an open end of the container 110. Optical elements 106, such as lenses, may be used to focus and/or direct incoming light in a desired manner. The container 110 is housed within or on the vehicle 102 (e.g., satellite or space capsule) and may be rotated (see, arrow of movement 112) into at least two positions: 1) to provide external viewing through the normal viewing direction; or 2) to provide light calibration through a calibration window 120. The calibration window 120 is preferably a thin window made of highly optically transmissive material for the frequencies of electromagnetic energy that are to be sensed by the sensor 108. The integrating sphere 134 is attached to or around the calibration window 120 through a gastight seal 132. In one embodiment, a pressurizing gas reservoir 114 provides a suitable gas or gas mixture through a regulator 116 into the integrated sphere 120 to maintain a specified gas pressure range. The regulator 116 preferably functions to remove, as well as to supply, gas to the sphere 134 to accommodate both increases and decreases in gas temperature changes and gas pressure changes caused by outgassing. Flexible power cables 130 for powering at least one source 128 of electromagnetic energy contained within the integrating sphere 134 are also supplied to the integrating sphere 134 through the vehicle 102. One or more processors (not shown) in the vehicle 102 drive control logic for the source of electromagnetic energy, and measure and regulate gas pressure in the integrating sphere 134.

The inflated integrating sphere 134 provides a proper environment for sources 128 of electromagnetic energy for calibration. Preferably, the ratio of the surface area of the integrating sphere 134 to an aperture area of the sensor 108 is at a maximum. The integrating sphere 134 preferably is at least double walled to provide sufficient insulation.

The integrating sphere 134 may be rigidified upon deployment to maintain a spherical shape longer under low internal gas pressure. The integrating sphere 134 may be hardened with a suitable hardening material, such as an injected fluid that solidifies within the skin or on the surface of the integrating sphere 134. In an embodiment, curable adhesive polymers may be injected between layers 124, 126 of the integrating sphere 134 upon deployment to bind the innermost and outermost layers 126, 124 and to help provide a rigid structure.

Figure 2:
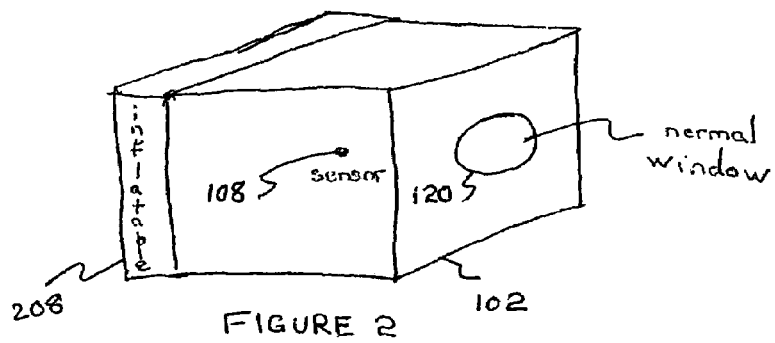
FIG. 2 shows a perspective view of an embodiment of a vehicle with an unexpanded integrating sphere.

FIG. 2 shows an embodiment of the vehicle 102 with the integrating sphere 134 packaged, folded, deflated, or collapsed. In this embodiment, the viewing window is opposite, rather than orthogonal to, the calibration window (not shown). The integrating sphere 134 is deployed (inflated or pressurized) in space where volume constraints are not as restrictive as during launch. Upon reaching an intended destination after launch, the integrating sphere 134 is inflated with a gas. The choice of the inflating gas is dependent upon the optical application and may include consideration as to whether the gas absorbs radiation in the spectral range of interest. A pressurizing gas that inflates the integrating sphere 134 is preferably very low absorbing in the spectral range of interest, inert or non-reactive, and has large gas molecules for easy sealing. Argon, Neon, and Krypton are examples of gas that may be used. The gas is regulated to the integrating sphere 134 to maintain the gas pressure to within a specified gas pressure range as long as a supply for the gas is not exhausted. It is contemplated that a gas mixture may be used and even a gas mixture in which at least one spectrally suitable component gas may be used to coat the interior of the integrating sphere 134 and aid the integrating sphere's ability to retain a spherical shape on its own. The gas pressure required to retain a spherical shape depends on the properties of the material chosen for the walls and on the environment where the integrating sphere 134 is deployed. In space borne or near vacuum conditions, a relatively small fluid pressure ($\leq 2$ pounds per square inch (psi)) keeps the integrating sphere spherical. Various materials, such as Mylar®, standard rubber, and latex, may be used for the integrating sphere 134. Because Mylar® doesn't stretch, less than one pound per square inch of pressure provides a fully inflated integrating sphere in a vacuum or near vacuum environment, as may be found in outer space. If a standard rubber or latex material is used, the expected pressure range to inflate the integrating sphere is about 1-2 psi.

Figure 8:
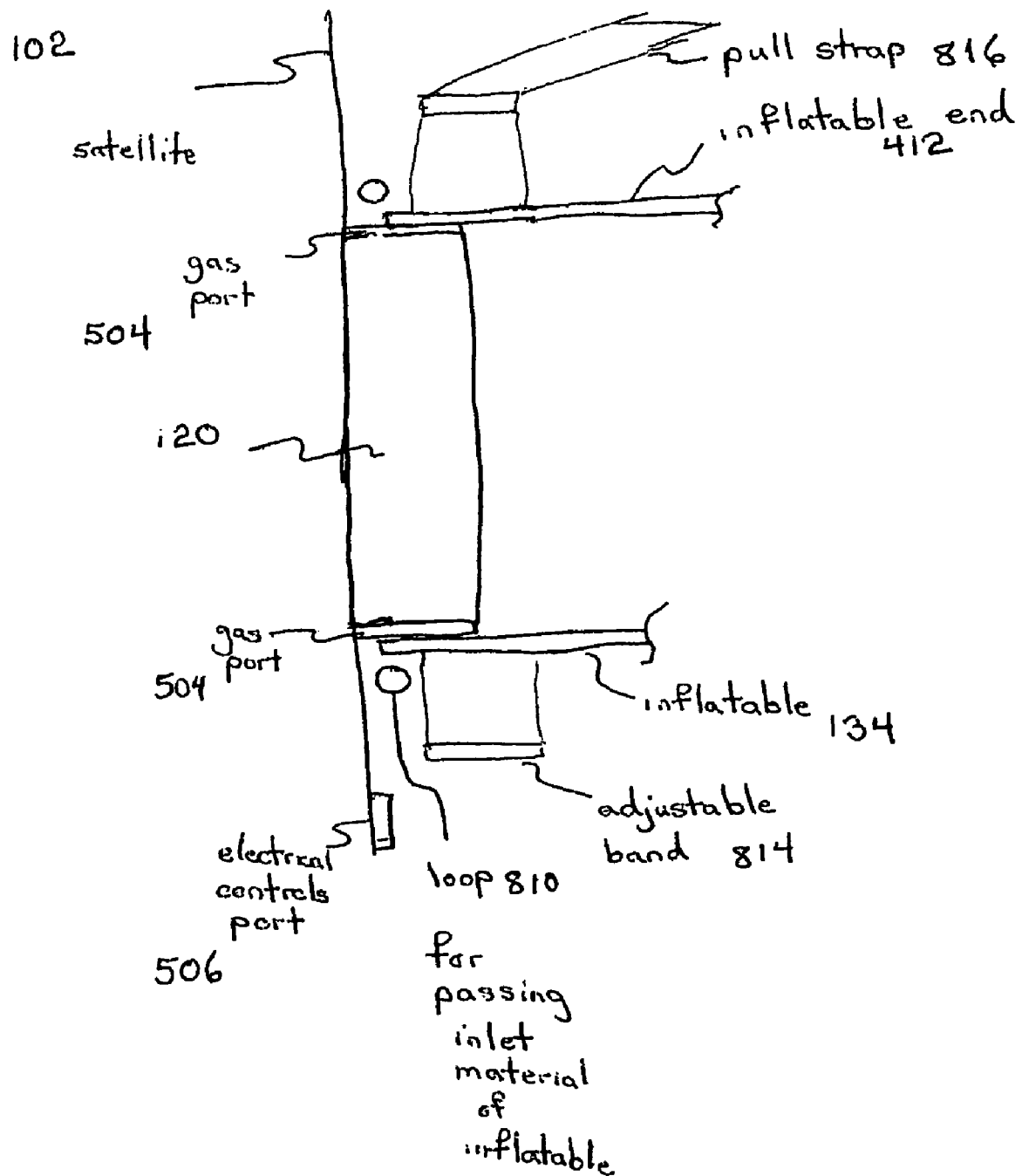
FIG. 8 shows an embodiment of a mechanism to secure the integrating sphere to the vehicle (e.g., instrument package or satellite)

FIG. 8 shows an embodiment of attaching the integrating sphere 134 to the vehicle 102. Preferably, a one-time deployable door (not shown) is used to protect the folded, deflated integrating sphere 134 until it is time to deploy the integrating sphere 134. Securing the integrating sphere to the vehicle is preferably accomplished through application of an adhesive around or in proximity to the exterior edge of the calibration window 120 and fitting an aperture of the integrating sphere 134 over the adhesive such that material of an interior of the integrating sphere at the aperture fits onto the adhesive. This material of the interior of the integrating sphere 134 may be formed as a lip from the aperture of the integrating sphere 134. Securing may further include applying a band 814 around the aperture of the integrating sphere 134 and tightening it through a pull strap 816. A loop 810 or partial loop may be provided to allow the end of the inflatable to be pulled over the loop to ensure that a sufficient amount of inflatable material is attached to the vehicle 102. Alternatively, or in addition, various glues and/or flanges, clamps, and O-rings may be used to hermetically secure the integrating sphere 134 to the vehicle 102. The gas port 504 may form a ring around or within the calibration window 120 or may be a simple outlet channel, such as a circular hole or passageway. The electrical controls port 506 preferably is a simple outlet channel in or near the calibration window 120.

Figure 3:
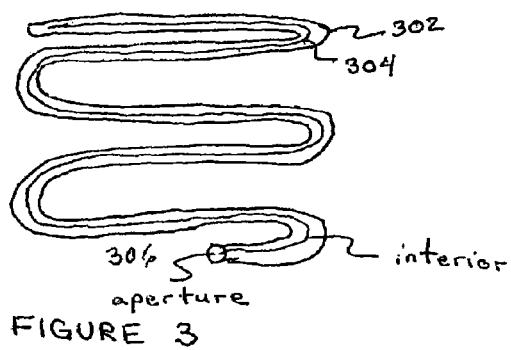
FIG. 3 shows an embodiment of a folded integrating sphere.
Figure 4:
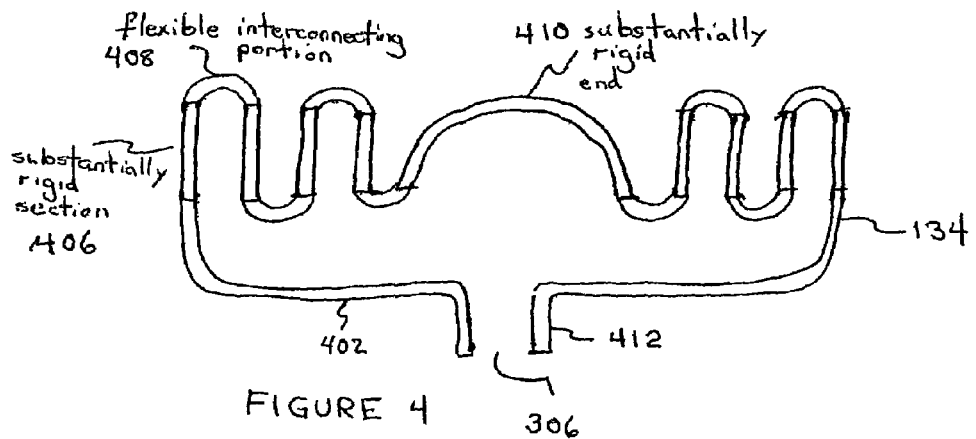
FIG. 4 shows an embodiment of an integrating sphere with substantially rigid sections.

Before deployment, the integrating sphere 134 is packed or otherwise reduced in volume. Packing may be accomplished in a variety of ways. Preferably, the deflated integrating sphere 304 is folded as shown cross sectionally in FIG. 3. In another embodiment, sections of the integrating sphere 134 may be substantially rigid with flexible interconnecting pieces 408 between rigid sections. FIG. 4 shows an example of such an embodiment. In the embodiment of FIG. 4, the rigid sections 406, 410 are curved sufficiently so as to be collapsible where the rigid sections fit into each other concentrically and expand to construct a spherical shape upon inflation. Rigid sections enhance the overall rigidity of the inflated structure. Integrating sphere material 134 extends out to form an extension 412 or lip around an aperture 306 through which a sensor 108 peers into the interior of a fully expanded integrating sphere 134.

Once the integrating sphere 134 is expanded in its environment of intended use, it becomes desirable to maintain the fluid pressure in the integrating sphere 134 at a desired level so as to maintain a spherical shape, while not also rupturing the material of the integrating sphere 134. If the fluid pressure in the integrating sphere 134 exceeds a maximum pressure threshold, the fluid is partially received by the supply 114 via regulator 116 so that the fluid remaining in the integrating sphere 134 is below the maximum pressure threshold. If the fluid pressure in the integrating sphere 134 becomes less than a minimum pressure threshold, the supply 114 provides more fluid to the integrating sphere 134 until the fluid pressure in the integrating sphere 134 is above the minimum pressure threshold. A fluid flow rate into the integrating sphere 134 upon inflation is set to minimize a risk of damage to the source or sources of electromagnetic energy 128.

Figure 5:
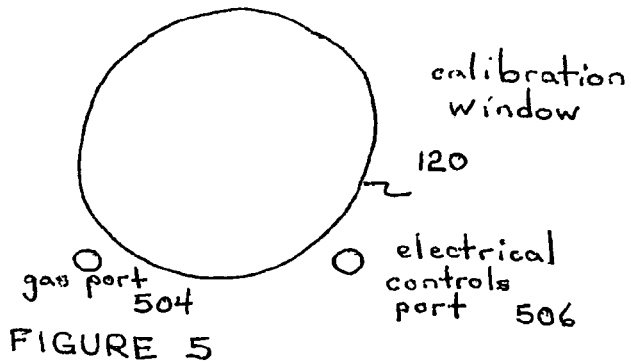
FIG. 5 shows an embodiment of a calibration window in relation to a gas port and an electrical controls port.

FIG. 5 shows an exemplary arrangement of the calibration window 120, gas port 504, and electrical controls port 506. Basically, when secured and inflated, the integrating sphere is maintained and used through three portals of the space capsule: the calibration window upon which or around which the integrating sphere is secured, a fluid (e.g., gas) port 504 that may be provided through the calibration window 120, around the calibration window 120, near the calibration window 120, or elsewhere depending upon system constraints; and an electrical controls port 506 that also may be disposed through, around, or near the calibration window 120 or located elsewhere.

Figure 6:
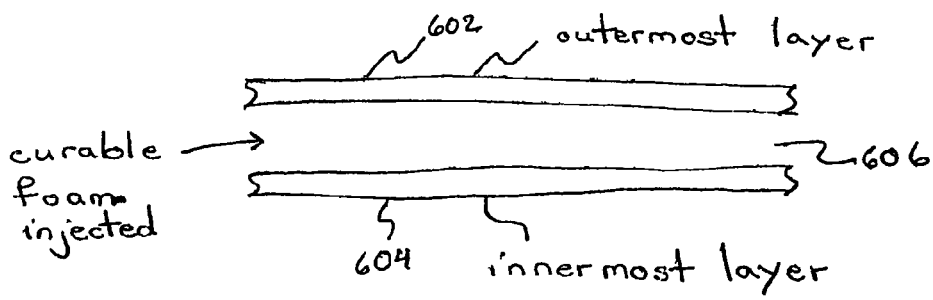
FIG. 6 shows a cutaway view of the skin of integrating sphere for an embodiment in which a solidifying adhesive is injected between the innermost and outermost layers.
Figure 7:
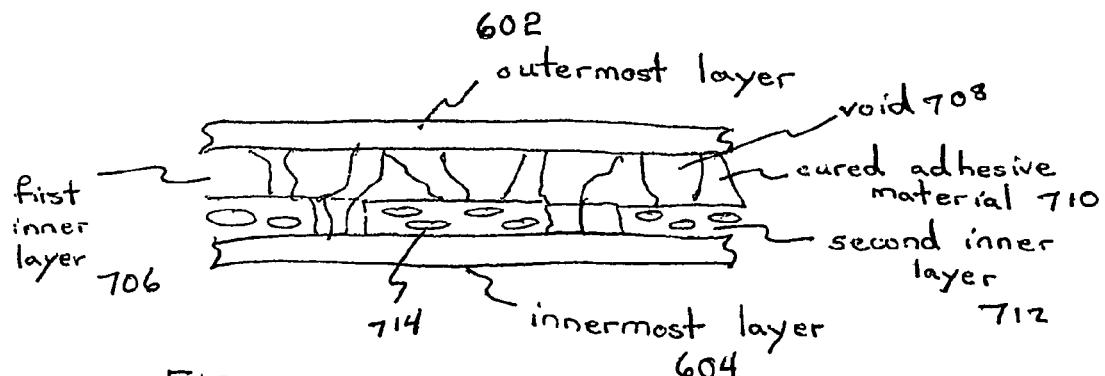
FIG. 7 shows a cutaway view of the skin of an integrating sphere for an embodiment in which two inner layers are disposed between the innermost and outermost layers.

The skin or exterior structure of the integrating sphere is preferably multilayered. The innermost layer is adapted for its optical properties and provides a diffusely reflective surface so as to provide maximum optical performance. For a visible light source, the innermost layer may be white; for infrared applications, the innermost layer may be gold coated. Preferably, the outermost layer is more mechanically specialized than the innermost layer and is gas impermeable and durable. For applications in which the integrating sphere is directly exposed to space, the outermost layer may be made sufficiently resistant to the effects of space dust. As shown in FIG. 6, a curable adhesive (e.g., a curable polymer that flows and sets) may be injected 606 between the innermost 604 and outermost layers 602 after the integrating sphere 134 is inflated to the proper pressure so as to provide a rigid structure and to act as an adhesive agent. Curing may occur through heating of the integrating sphere by exposure to solar radiation. FIG. 7 shows an alternate embodiment in which two layers are provided between the innermost layer 702 and the outermost layer 704. In this embodiment, the first inner layer 706 is a porous adhesive layer, formed of cured adhesive material 710 and voids 708, for binding the innermost and outermost layers and the second inner layer 712 is a self healing layer. The second inner layer 712 may contain pockets 714 of liquefied resin that cure upon release from the pocket containing it; in effect, this layer would act as a self healing layer to act to prevent against gas loss in case of puncture or tears. Although the present invention may be implemented without any active thermal control, in an embodiment, a layer may be included as a thermally conductive mesh to provide heating to all or part of the surface of the integrating sphere. In addition, or as an alternative, spray nozzles on the vehicle that spray a rigidifying substance onto the integrating sphere as the sphere is inflated may be located on the vehicle.

The interior of the integrating sphere has at least one source of electromagnetic energy 128. Usually, the source 128 provides visible light, infrared light, or ultraviolet light. Electronics onboard the space capsule or satellite may store appropriate data regarding the effects of duration of use and aging on the performance of the source to more accurately perform any calibration measurements. For a calibration operation, a source of electromagnetic energy 128 is turned on within the interior of the integrating sphere 134. Optionally, a second source of electromagnetic energy within the interior of the integrating sphere is turned on upon detecting a failure in the first source of electromagnetic energy. Additional sources of electromagnetic energy may be provided. Multiple light sources may be used for redundancy, in a method to calibrate the calibrating light source or each other, or to provide different spectra. The frequency of calibration is determined by the specifics of the sensor 108 employed and its application. In one embodiment, each of the multiple light sources 128 has a unique center frequency of electromagnetic energy emitted; for example, red, green, and blue light emitting lamps.

Figure 9:
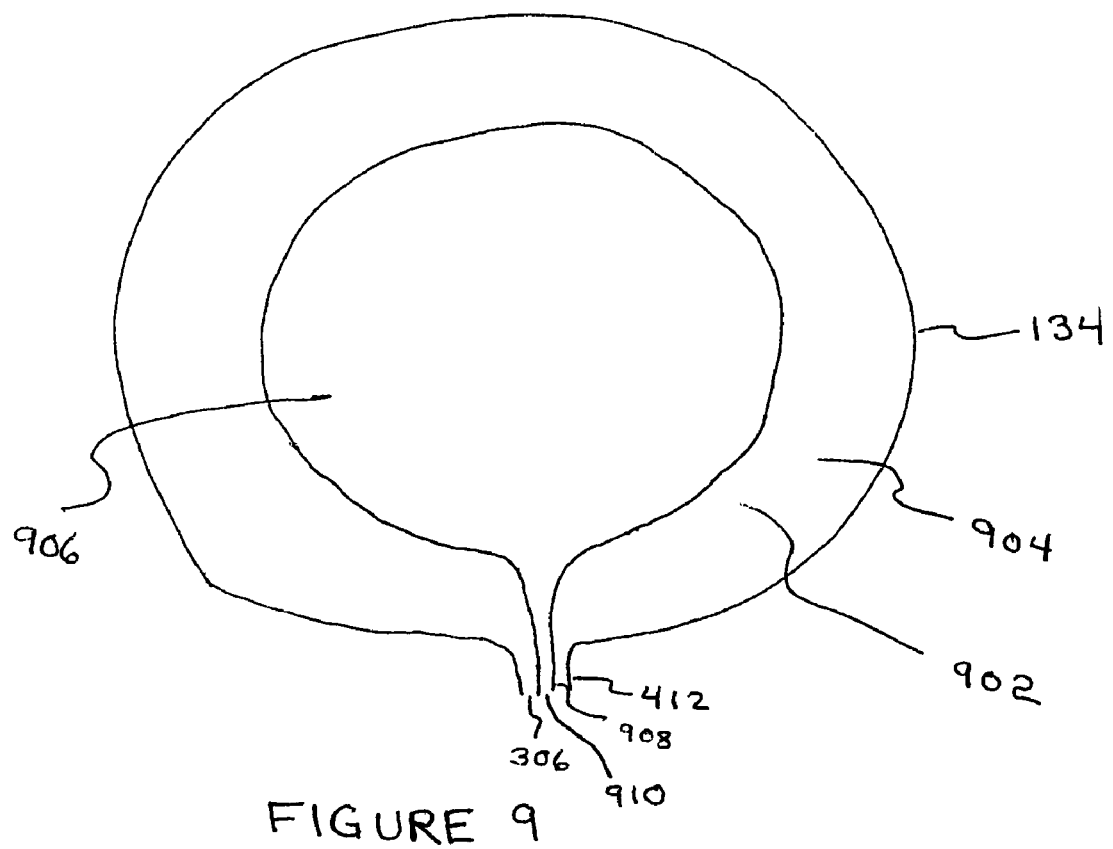
FIG. 9 shows an embodiment of an integrating sphere having an exterior chamber and an interior chamber.

FIG. 9 illustrates an embodiment in which the integrating sphere 134 has a concentric multichambered arrangement of an interior chamber 906 defined by a surface or skin 906 essentially surround by an exterior chamber 904. Each chamber may be inflated/deflated through concentric apertures 306 and 910 defined through interior surface lip 908 and exterior surface lip (i.e., integrating sphere lip) 412. In one embodiment, a gas filling the exterior chamber is different from the gas filling the interior chamber. One of the filing gases may be UV radiation absorptive and the other filing gas may be UV radiation transmissive. The interior chamber need not be gas filled, but may be liquid filled or, possibly, a solid.

Thus, the present invention has been described herein with reference to a particular embodiment for a particular application. modifications, applications, and embodiments within the scope thereof. Although the term "vehicle" has been employed, it is to be understood that other embodiments may include those having stationary instrumentation. Although selected embodiments have been illustrated and described in detail, it will be understood that various substitutions and alterations are possible. Those having ordinary skill in the art and access to the present teachings will recognize additional various substitutions and alterations are also possible without departing from the spirit and scope of the present invention, and as defined by the following claims.

I claim:

1. An optical integrating sphere, comprising:
   a structure that expands to provide a generally spherical shape, the structure having an open interior when expanded, characterized by a reflective surface; and
   a source of electromagnetic energy to illuminate the interior of the expandable structure.

2. An optical integrating sphere as in claim 1, wherein the source of electromagnetic energy is located within the expandable structure.

3. An optical integrating sphere as in claim 1, wherein the source of electromagnetic energy comprises at least one light source.

4. An optical integrating sphere as in claim 3, wherein at least two of the light sources have a unique center frequency of emitted electromagnetic energy.

5. An optical integrating sphere as in claim 1, wherein the expandable structure comprises at least two layers including an innermost layer and an outermost layer.

6. An optical integrating sphere as in claim 1, wherein the expandable structure is foldable.

7. An optical integrating sphere as in claim 1, wherein the expandable structure had substantially rigid sections and substantially flexible portions interconnecting the substantially rigid sections.

8. An optical integrating sphere as in claim 7, wherein the rigid sections are collapsible into a concentric form.

9. An optical integrating sphere as in claim 5, wherein the outermost layer is impermeable.

10. An optical integrating sphere as in claim 9, further comprising an inner layer between the outermost and innermost layers.

11. An optical integrating sphere as in claim 10, wherein the inner layer allows for an adhesive to be injected between the innermost and outermost layers.

12. An optical integrating sphere as in claim 11, wherein the adhesive forms a bond and rigidifies over time.

13. An optical integrating sphere as in claim 10, the said inner layer being a first inner layer, further comprising a second inner layer.

14. An optical integrating sphere as in claim 13, wherein the first inner layer is a porous adhesive layer for binding the innermost and outermost layers and the second inner layer is a self healing layer.

15. An optical integrating sphere as in claim 14, wherein the second inner layer contains pockets of liquefied resin that cure upon release.

16. An optical integrating sphere as in claim 1, wherein the expandable structure is expanded outside the earth's atmosphere.

* * * * *